United States Patent
Arava et al.

(10) Patent No.: US 9,783,506 B2
(45) Date of Patent: Oct. 10, 2017

(54) PROCESS FOR THE LARGE SCALE PRODUCTION OF 1H-[1,2,3]TRIAZOLE AND ITS INTERMEDIATE 1-BENZYL-1H-[1,2,3]TRIAZOLE

(71) Applicant: SUVEN LIFE SCIENCES LIMITED, Hyderabad, Andhra Pradesh (IN)

(72) Inventors: Veera Reddy Arava, Hyderabad (IN); Sashibhushan Malreddy, Hyderabad (IN); Chalapathi Lagupudi, Hyderabad (IN); Venkateswarlu Jasti, Hyderabad (IN)

(73) Assignee: SUVEN LIFE SCIENCES LIMITED, Hyderabad (IN)

( * ) Notice: Subject to any disclaimer, the term of this patent is extended or adjusted under 35 U.S.C. 154(b) by 0 days.

(21) Appl. No.: 14/912,081

(22) PCT Filed: Jan. 27, 2014

(86) PCT No.: PCT/IN2014/000062
§ 371 (c)(1),
(2) Date: Feb. 12, 2016

(87) PCT Pub. No.: WO2015/037013
PCT Pub. Date: Mar. 19, 2015

(65) Prior Publication Data
US 2016/0200691 A1    Jul. 14, 2016

(30) Foreign Application Priority Data
Sep. 13, 2013  (IN) ............................ 4132/CHE/2013

(51) Int. Cl.
C07D 249/04 (2006.01)

(52) U.S. Cl.
CPC .................... *C07D 249/04* (2013.01)

(58) Field of Classification Search
CPC ..................... C07D 249/04; C07D 249/06
See application file for complete search history.

(56) References Cited

PUBLICATIONS

Karger, updated 2011, retrieved Jan. 4, 0217 from https://www.britannica.com/science/separation-and-purification.*
Farooq, 2012, Synthesis, vol. 44, No. 13, p. 2070-2078.*
Dallinger, 2011, Org. Process Res. Dev., vol. 15, p. 841-854.*
European Patent Office, "International Search Report", dated May 8, 2014 in PCT Application No. PCT/IN2014/000062.
European Patent Office, "International Preliminary Report on Patentability", dated Oct. 30, 2015 in PCT Application No. PCT/IN2014/000062.
European Patent Office, "Written Opinion of the International Preliminary Examining Authority", dated Aug. 25, 2015 in PCT Application No. PCT/IN2014/000062.
European Patent Office, "Written Opinion of the International Searching Authority", dated May 8, 2014 in PCT Application No. PCT/IN2014/000062.
Hansen et al., "Microwave irradiation as an effective means of synthesizing unsubstituted N-linked 1,2,3-triazoles from vinyl acetate and azides" SYNLETT 20:3275-78 (2009).
A.C. Tome, "Product Class 13: 1,2,3-triazoles" Science of Synthesis. 13:415-601 (2004) XP008091244.
Wu et al., "A Convenient Synthesis of 1-Substituted 1,2,3-Triazoles via CuI/Et3N Catalyzed 'Click Chemistry' from Azides and Acetylene Gas" Synlett 9:1453-56 (2009).
Hansen et al., "Supporting Information" for:Microwave irradiation offers an effective means for the synthesis of unsubstituted N-Linked 1,2,3-triazoles from vinyl acetate and azides. SYNLETT 20:3275-78 (2009); as marked at p. 3277, Supporting Information obtained from http://www.thieme-connect.com/ejournals/toc/synlett.

* cited by examiner

*Primary Examiner* — Rebecca Anderson
*Assistant Examiner* — Karen Cheng
(74) *Attorney, Agent, or Firm* — Iphorgan Ltd.

(57) ABSTRACT

The present invention provides a process for the large scale production of 1H-[1,2,3]triazole of formula (I) and its intermediate 1-benzyl-1H-[1,2,3]triazole of formula (II) by using benzyl azide and vinyl acetate as starting materials. This process is economical, environment friendly and safer by avoiding use of special equipment.

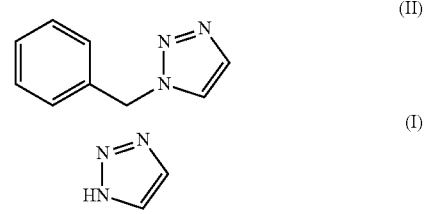

7 Claims, No Drawings

PROCESS FOR THE LARGE SCALE PRODUCTION OF 1H-[1,2,3]TRIAZOLE AND ITS INTERMEDIATE 1-BENZYL-1H-[1,2,3]TRIAZOLE

CROSS REFERENCE TO RELATED APPLICATIONS

This application is a national stage completion application of PCT Application No. PCT/IN2014/000062, filed Jan. 27, 2014, and claims the benefit of Indian Application No. 4132/CHE/2013, filed Sep. 13, 2013. Each of these applications is incorporated by reference herein in its entirety.

FIELD OF THE INVENTION

The present invention provides process for the large scale production of 1H-[1,2,3]triazole of formula (I) and it's intermediate 1-benzyl-1H-[1,2,3]triazole of formula (II) by using benzyl azide and vinyl acetate as starting materials. This process is economical, environment friendly and safer by avoiding use of special equipment.

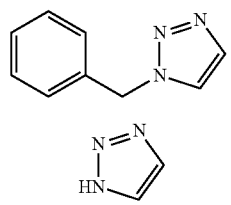

(II)

(I)

BACKGROUND OF THE INVENTION

N-Substituted 1,2,3-triazoles are useful as dyestuffs, photo stabilizers, corrosion inhibitors, pharmaceutical and agrochemicals. 1H-[1,2,3]-triazole is used as major intermediate in the synthesis of N-substituted 1,2,3-triazoles. Hence, the demand for 1H-[1,2,3]-triazole is increasing very heavily now-a-days (Science of Synthesis, 2004, 13, 415-601).

1H-[1,2,3]-triazole is usually prepared by the addition of benzylazide to acetylene in the presence of copper catalyst and under pressure to obtain 1-benzyl-1H-[1,2,3]triazole. 1-Benzyl-1H-[1,2,3]triazole is then debenzylated in presence of Pd—C to obtain 1,2,3-triazole (Synlett, 2009, 9, 1453-1456).

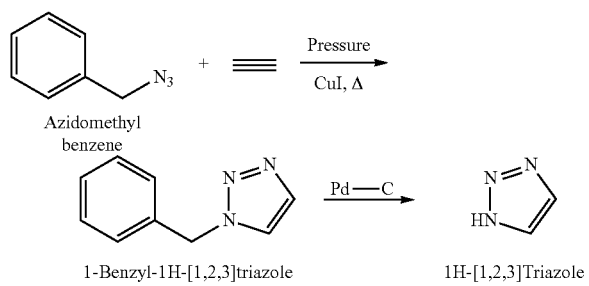

The drawback of the above procedure for commercialization is that it involves pressure reaction of azidomethyl benzene with acetylene, which is exothermic in nature and needs special equipment and attention during large scale production.

Hence, there is a need for a viable process, for the production of 1H-[1,2,3]-triazole and its intermediate 1-benzyl-1H-[1,2,3]triazole on a larger scale, which is both safe and economical and does not require special equipment.

SUMMARY OF THE INVENTION

In one aspect, the present invention relates to large scale production of 1-benzyl-1H-[1,2,3]triazole of formula (II), which is useful for the preparation of 1H-[1,2,3]triazole of formula (I).

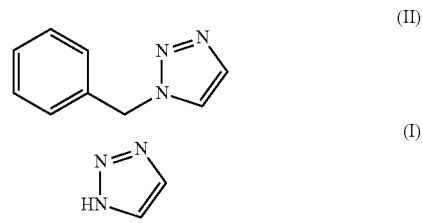

The process involves the following steps:

Step (i): Benzyl azide of formula (A) is reacted with vinyl acetate of formula (B) in a closed vessel, at a temperature in the range of 110° C. to 130° C., for the period of 9 hours to 16 hours to obtain 1-benzyl-1H-[1,2,3]triazole of formula (II);

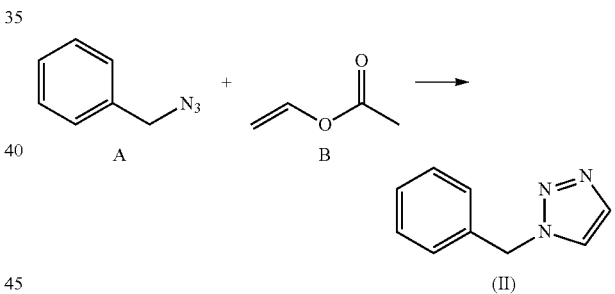

Step (ii): 1-Benzyl-1H-[1,2,3]triazole of formula (II) is purified by crystallization in presence of a suitable solvent to obtain high quality product, 1-benzyl-1H-[1,2,3]triazole of formula (II).

In another aspect, the present invention relates to large scale production of 1H-[1,2,3]triazole of formula (I).

The process involves the following steps:

Step (i): Benzyl azide of formula (A) is reacted with vinyl acetate of formula (B) in a closed vessel, at a temperature in the range of 110° C. to 130° C. for the period of 9 hours to 16 hours to obtain 1-benzyl-1H-[1,2,3]triazole of formula (II);

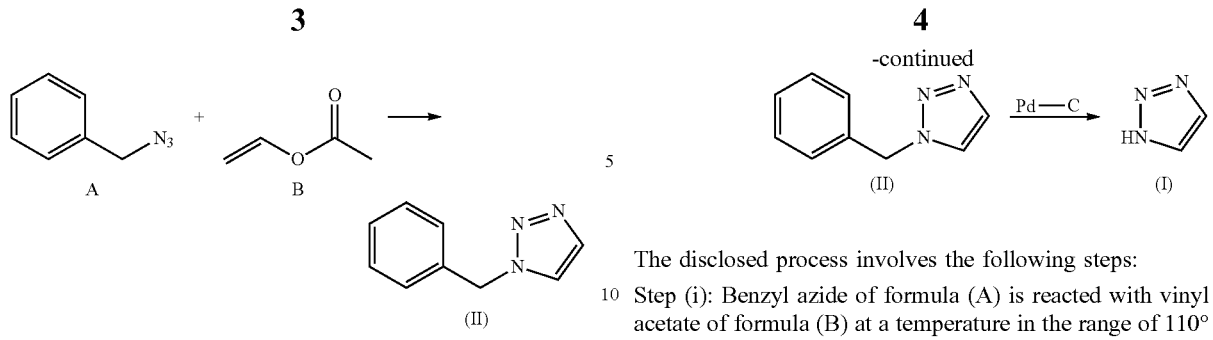

Step (ii): 1-Benzyl-1H-[1,2,3]triazole of formula (II) is purified by crystallization in presence of a suitable solvent to obtain high quality 1-benzyl-1H-[1,2,3]triazole of formula (II);

Step (iii): 1-Benzyl-1H-[1,2,3]triazole of formula (II) is debenzylated with Pd—C in presence of suitable solvent at a temperature in the range of 100° C. to 120° C. for the period of 8 hours to 14 hours to obtain crude 1H-[1,2,3]-triazole of formula (I). This crude product was purified by high vacuum distillation to yield high quality 1H-[1,2,3] triazole of formula (I).

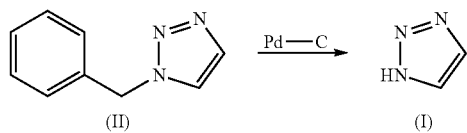

In another aspect, the present invention relates to large scale, well optimized manufacturing process for 1H-[1,2,3] triazole of formula (I) and its intermediate 1-benzyl-1H-[1,2,3]triazole of formula (II).

In another aspect, the present invention relates to process for large scale production of 1H-[1,2,3]triazole of formula (I) and its intermediate 1-benzyl-1H-[1,2,3]triazole of formula (II) in a safer way, avoiding special equipments.

In yet another aspect, the present invention relates to large scale, economical production of 1H-[1,2,3]triazole of formula (I) and it's intermediate 1-benzyl-1H-[1,2,3]triazole of formula (II).

In still yet another aspect, the present invention provides a process to obtain the product, 1H-[1,2,3]triazole of formula (I) and it's intermediate 1-benzyl-1H-[1,2,3]triazole of formula (II) in substantially pure forms.

DETAILED DESCRIPTION OF THE INVENTION

The large scale manufacturing process for the preparation of 1H-[1,2,3]triazole of formula (I) and it's intermediate, 1-benzyl-1H-[1,2,3]triazole of formula (II) is illustrated by the Scheme-I given below:

Scheme-I

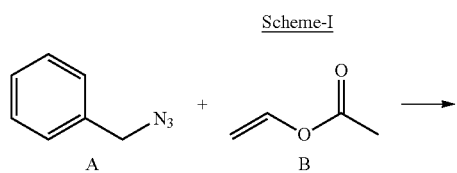

The disclosed process involves the following steps:

Step (i): Benzyl azide of formula (A) is reacted with vinyl acetate of formula (B) at a temperature in the range of 110° C. to 130° C. for the period of 9 hours to 16 hours to obtain 1-benzyl-1H-[1,2,3]triazole of formula (II);

Step (ii): 1-benzyl-1H-[1,2,3]triazole of formula (II) is purified by distillation in presence of suitable solvent to obtain high quality 1-benzyl-1H-[1,2,3]triazole of formula (II);

Step (iii): 1-benzyl-1H-[1,2,3]triazole of formula (II) is debenzylated with Pd—C in presence of suitable solvent at a temperature in the range of 100° C. to 120° C. for the period of 8 hours to 14 hours to yield crude 1H-[1,2,3] triazole of formula (I). The crude product, thus obtained, was purified by high vacuum distillation to yield high quality 1H-[1,2,3]-triazole of formula (I).

In the first step of the preparation, benzyl azide of formula (A) is reacted with vinyl acetate of formula (B) to obtain 1-benzyl-1H-[1,2,3]triazole of formula (II). The reaction temperature may range from 110 to 130° C. and preferably at a temperature of 120° C. The duration of the reaction may range from 9 to 16 hours, preferably for the period of 14 hours.

In the second step of the preparation, 1-benzyl-1H-[1,2,3]triazole of formula (II) is purified by distillation in presence of suitable solvent to obtain high quality 1-benzyl-1H-[1,2,3]triazole of formula (II). The suitable solvent is preferably ethyl acetate and hexane.

In the third step of the preparation, 1-benzyl-1H-[1,2,3] triazole of formula (II) is debenzylated with Pd—C to yield crude 1H-[1,2,3]-triazole of formula (I). This is purified by high vacuum distillation to obtain high quality 1H-[1,2,3] triazole of formula (I). The reaction temperature may range from 100° C. to 120° C. and preferably at a temperature of 110° C. The duration of the reaction may range from 8 to 14 hours, preferably from a period of 10 to 12 hours.

The details of the invention are given in examples provided below, which are given only to illustrate the invention and therefore should not be construed to limit the scope of the present invention.

Preparation 1: Preparation of 1-Benzyl-1H-[1,2,3]triazole

Benzyl triethyl ammonium chloride (2.4 Kgs, 10.53 moles), triethylamine hydrochloride (2.4 Kgs, 17.35 moles) were added to benzyl chloride (100 Kgs, 78.74 moles) at 50° C. over a period of 10 minutes. Sodium azide (54 Kgs, 83.07 moles) was added portion wise over a period of 3 hours at 50-55° C. (the reaction is highly exothermic) and maintained for 5 to 8 hours at the same temperature. Upon completion of the reaction (benzyl chloride should be less than 0.5% by Gas Chromatography), the mass was cooled to room temperature and maintained at the same temperature for 30 minutes. The salt was filtered and washed with vinyl acetate (2×50 Lts). The resulting filtrate (150 Kgs, including vinyl acetate) is employed directly for the next stage.

Example 1: Preparation of 1H-[1,2,3]triazole

Step (i): Preparation of 1-Benzyl-1H-[1,2,3]triazole

The filtrate obtained from preparation 1 is mixed with fresh vinyl acetate (200 Kg) in a closed vessel reactor at room temperature. Reaction mass heated to 120° C. and maintained for 10 to 14 hours (6-8 Kgs pressure was observed initially). After completion of the reaction (benzyl azide content should be less than 0.5% maintained by Gas Chromatography), cooled to 20° C. and unloaded the mass. Then distilled out the vinyl acetate under atmospheric pressure until the temperature reaches to 120° C. and finally applied high vacuum to collect the traces of vinyl acetate below 80° C. to obtain the crude product (132 Kgs).

Step (ii): Purification of 1-Benzyl-1H-[1,2,3]triazole

A suspension of 1-Benzyl-1H-[1,2,3]triazole (100-105 Kgs, obtained in the above step) in ethyl acetate (80 Lts) was heated to 45-50° C. and maintained for 15 minutes to obtain a clear solution. After getting clear solution, hexane (160 Lts) was added at 35° C. and maintained the resulting slurry for 60 minutes. Reaction mass was further cooled and maintained for 1 hour at 0-5° C. Then the mass was filtered and washed the cake with hexane (25 Lts) to obtain pure compound (90 Kgs).

$^1$H-NMR (CDCl$_3$-TMS, δ ppm): 7.63 (s, 1H), 7.47 (s, 1H), 7.29 (m, 5H), 5.49 (s, 2H);
$^{13}$C-NMR (CDCl$_3$-TMS, δ ppm): 134.67, 134.04, 128.96, 128.93, 127.86, 123.39, 53.75;
Mass (m/z): 160.2[M+1].

Example 2: Preparation of 1H-[1,2,3]triazole

1-Benzyl-1H-[1,2,3]triazole (125 Kgs, obtained in the Example 1) in isopropyl alcohol (500 Lts) was hydrogenated with 3.75 Kgs of 5% Pd—C under a pressure of 20-25 Kgs at 110° C. for 10 to 12 hours. At end of the reaction, benzyl triazole content was 1.66% and triazole content was 98.34%. The reaction mass was cooled to room temperature and filtered Pd—C through hyflo bed and washed the bed with isopropanol (100 Lts). Distilled off the solvent under vacuum completely to obtain the crude product, 1H-[1,2,3] triazole (78 Kgs). The crude material, thus obtained, was purified by high vacuum distillation (2-5 mm) and collected the pure title compound (38-42 Kgs) at vapor temperature (80-83° C.).

$^1$H-NMR (CDCl$_3$, δ ppm): 15.24 (s, 1H), 7.69 (s, 2H);
$^{13}$C-NMR (CDCl$_3$, δ ppm): 129.47

Advantages of the Invention

1. This process is very simple and starts from the readily available starting material which makes the process economical and industrially viable.
2. Vinyl acetate is easy to handle, compared to other acetylene equivalents and it is substantially a cheaper starting material.
3. The process does not involve handling of acetylene gas, therefore no need of special attention to control in plant scale.

We claim:
1. A process for the large scale production of 1H-[1,2,3]-triazole of formula (I),

which comprises of the following steps:
Step (i): reacting benzyl azide of formula (A) with vinyl acetate of formula (B) in a closed vessel reactor, at a temperature in the range of 110° C. to 130° C., for the period of 9 hours to 16 hours to obtain the product, 1-benzyl-1H-[1,2,3]triazole of formula (II);

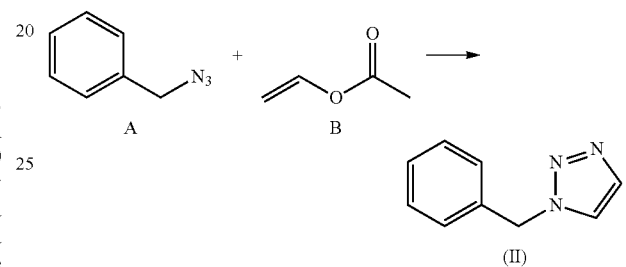

Step (ii): purifying 1-benzyl-1H-[1,2,3]triazole of formula (II) by crystallization in presence of a suitable solvent to obtain a high quality product, 1-benzyl-1H-[1,2,3]triazole of formula (II);
Step (iii): debenzylating 1-benzyl-1H-[1,2,3]triazole of formula (II) with Pd—C in presence of suitable solvent in a closed vessel reactor, at a temperature in the range of 100° C. to 120° C. for the period of 8 hours to 14 hours to obtain crude 1H-[1,2,3]triazole of formula (I) and purifying the crude product by high vacuum distillation to obtain 1H-[1,2,3]triazole of formula (I)

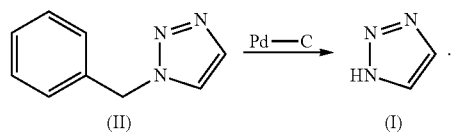

2. The process as claimed in step (iii) of claim 1, wherein the reaction is carried out at temperature of 110° C.
3. The process as claimed in step (iii) of claim 1, wherein the reaction is carried out for the period of 10 hours to 12 hours.
4. The process as claimed in step (i) of claim 1, wherein the reaction is carried out at temperature of 120° C.
5. The process as claimed in step (i) of claim 1, wherein the reaction is carried for the period of 14 hours.
6. The process as claimed in step (ii) of claim 1, wherein the suitable solvent is ethyl acetate and hexane.
7. The process as claimed in step (iii) of claim 1, wherein said suitable solvent is isopropyl alcohol.

* * * * *